(12) United States Patent
Chen et al.

(10) Patent No.: US 7,994,358 B2
(45) Date of Patent: Aug. 9, 2011

(54) PHOSPHORUS-CONTAINING COMPOUND AND METHOD FOR PREPARING THE SAME

(75) Inventors: Gai-Chi Chen, Taipei (TW); Ching-Jui Huang, Taipei (TW); An Pang Tu, Taipei (TW); Kuen Yuan Hwang, Taipei (TW)

(73) Assignee: Chang Chun Plastic Co., Ltd., Taipei (TW)

( * ) Notice: Subject to any disclaimer, the term of this patent is extended or adjusted under 35 U.S.C. 154(b) by 114 days.

(21) Appl. No.: 12/575,126

(22) Filed: Oct. 7, 2009

(65) Prior Publication Data

US 2010/0105939 A1 Apr. 29, 2010

(30) Foreign Application Priority Data

Oct. 23, 2008 (TW) .............................. 97140590 A

(51) Int. Cl.
*C07F 9/655* (2006.01)
(52) U.S. Cl. ........................................... 558/82
(58) Field of Classification Search .................. None
See application file for complete search history.

(56) References Cited

U.S. PATENT DOCUMENTS 4,618,693 A 10/1986 Saito et al.
6,441,067 B1 * 8/2002 Chiu et al. ................... 524/117

* cited by examiner

*Primary Examiner* — Yong Chu
*Assistant Examiner* — Michael Barker
(74) *Attorney, Agent, or Firm* — Edwards Angell Palmer & Dodge LLP; Peter F. Corless

(57) ABSTRACT

The present invention provides a phosphorus-containing compound of formula (I):

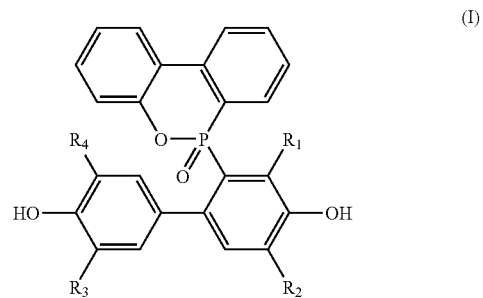

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy. The phosphorus-containing compound is prepared by bonding a bisphenol group to a phosphorus atom to prevent the phosphorus-containing heterocyclic molecule from exhibiting steric hindrance on hydroxyl functional groups, thereby increasing reactivity in the subsequent reactions.

19 Claims, 2 Drawing Sheets

PHOSPHORUS-CONTAINING COMPOUND AND METHOD FOR PREPARING THE SAME

FIELD OF THE INVENTION

The present invention relates to phosphorus-containing compounds and methods for preparing the same, and more particularly, to a phosphorus-containing compound exhibiting less steric hindrance and a method for preparing the same.

DESCRIPTION OF RELATED ART

Since epoxy resin composite materials have two or more reactive epoxide functional groups present in their structures, they exhibit excellent reactivity, toughness and flexibility. In addition, epoxy resin composite materials can be simply processed, and have high safety and superior mechanical and chemical properties, such that they are widely applied to coatings, electrical insulations, construction materials, adhesives, and laminates.

U.S. Pat. No. 4,618,693 discloses an organic phosphorus compound, which is useful as flame retardant and is prepared by reacting 9,10-dihydro-9-oxa-10-phosphaphenanthrene-10-oxide (DOPO) (as a raw material for synthesizing a flame retardative resin) with 1,4-benzoquinone (BQ) to obtain 10-(2',5'-dihydrophenyl)-9,10-dihydro-9-oxa-10-phosphaphenanthrene-10-oxi de (DOPO-BQ). DOPO-BQ has a polycyclic ring in its molecular structure, so that a high char yield is obtained. As a result, DOPO-BQ exhibits excellent resistance to burning, and thus it can be used as a flame retardant. Furthermore, DOPO-BQ has two hydroxyl functional groups, such that it can also be used as a starting material for producing a variety of resins. For example, it can be used as reactant in preparing epoxy resins.

However, the hydroxyl functional groups of DOPO-BQ are located in a benzene ring with a smaller molecular size, and thus DOPO with a larger molecular size tends to exhibit steric hindrance reactivity which adversely affects reactivity during syntheses of resins.

Therefore, there exists an urgent need to develop a phosphorus-containing compound exhibiting less steric hindrance to facilitate preparation of a flame retardative epoxy resin.

SUMMARY OF THE INVENTION

In order to solve the aforesaid problems, it is an aspect of the present invention to provide a phosphorus-containing compound exhibiting less steric hindrance.

In order to achieve the above and other aspects, the present invention provides a phosphorus compound of formula (I):

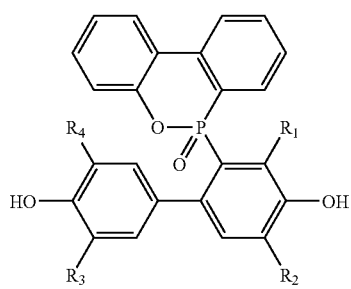

(I)

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy.

The present invention further provides a method for preparing a phosphorus-containing compound of formula (I), comprising the step of:

reacting a compound of formula (II):

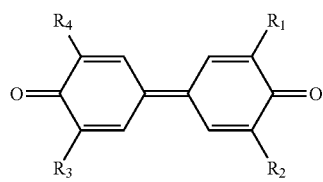

(II)

with a compound (DOPO) of formula (III):

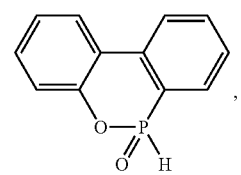

(III)

in the presence of a catalyst and an organic solvent, to obtain a phosphorus-containing compound of formula (I):

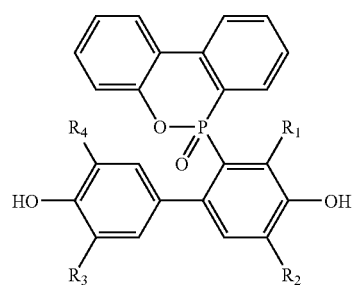

(I)

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy.

In the present invention, the steric hindrance exhibited by the DOPO molecule on the hydroxyl functional groups is avoided by linking a bisphenol group to the DOPO molecule, thereby increasing the reactivity in the subsequent reaction steps.

BRIEF DESCRIPTION OF DRAWINGS

The present invention can be more fully understood by reading the following detailed description of the preferred embodiments, with reference made to the accompanying drawings, wherein.

DETAILED DESCRIPTION OF PREFERRED EMBODIMENTS

Figure 1:
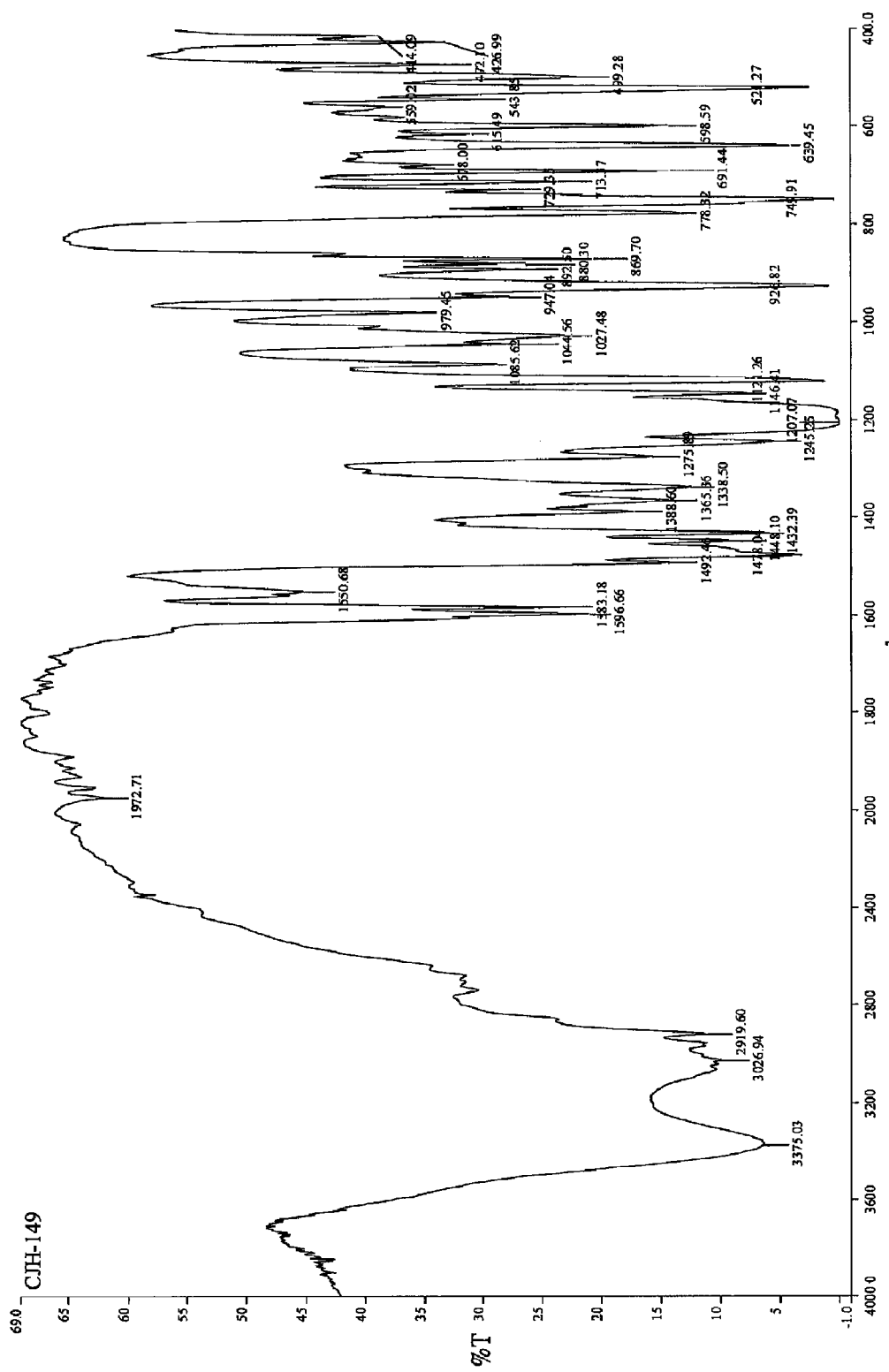
FIG. 1 is an infrared (IR) spectrum of a phosphorus-containing compound of formula (I) according to the present invention.

Preferred embodiments of a phosphorus-containing compound proposed in the present invention are described as follows with reference to FIGS. 1 and 2. Persons having ordinary skills in the art should be able to easily appreciate the other advantages and effects of the present invention based on the disclosure of the specification.

The present invention provides a phosphorus-containing compound of formula (I):

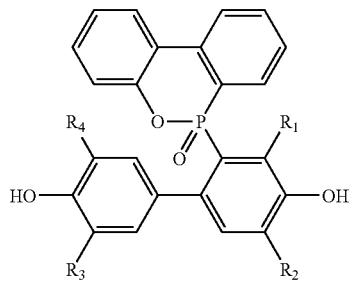

(I)

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy.

In a preferred embodiment of the present invention, $R_1$, $R_2$, $R_3$ and $R_4$ are preferably $C_{1-8}$ alkyl, and $R_1$, $R_2$, $R_3$ and $R_4$ are more preferably methyl. In order to obtain a phosphorus-containing compound of formula (I), the present invention further provides a method for preparing a phosphorus-containing compound of the formula (I), comprising the step of:

reacting a compound of formula (II):

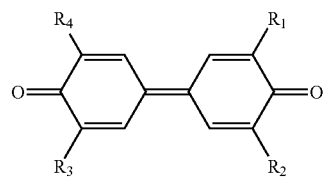

(II)

with a compound of formula (III):

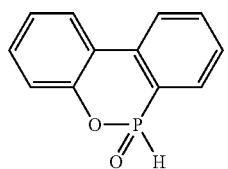

(III)

in the presence of a catalyst and an organic solvent, to obtain a phosphorus-containing compound of formula (I):

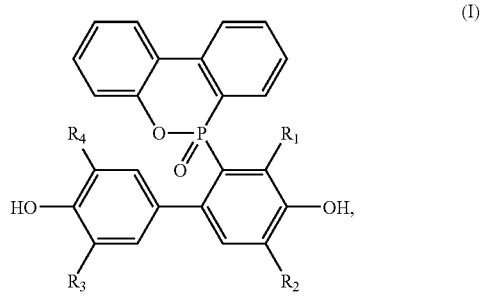

(I)

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy.

In the method of the present invention, the catalyst used is an alkaline catalyst, including, but not limited to, triethylamine, tripropylamine, triphenylphosphine, potassium tert-butoxide (KOt-Bu), and 1,8-diazabicyclo[5.4.0]undec-7-ene. In an embodiment of the present invention, the catalyst is triethylamine.

Moreover, the compound of formula (II) and/or the compound of formula (III) are dissolved in an organic solvent before reacting the compounds of formulae (II) and (III) with each other. Examples of the organic solvent include, but not limited to, toluene, dichloromethane, trichloromethane, tetrahydrofuran, xylene, benzene, and N,N-dimethylformamide. Further, a single solvent or mixed solvents may be optionally used. Thus, the organic solvent of the present invention may include one or more solvents selected from the group consisting of toluene, dichloromethane, trichloromethane, tetrahydrofuran, xylene, benzene, and dimethylformamide.

In the method of the present invention, the compounds of formulae (II) and (III) react each other for 1 to 4 hours at a temperature of 25 to 100° C., and preferably 30 to 50° C.

In the method of the present invention, a compound of formula (IV):

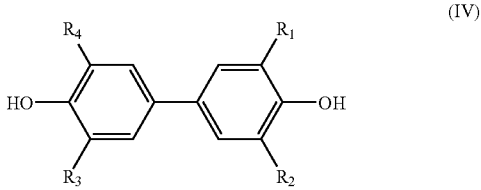

(IV)

is oxidized for 3 to 8 hours, in the presence of a copper halide catalyst, to obtain a compound of formula (II).

In another embodiment of the present invention, the compound of formula (IV) is oxidized for 3 to 4 hours, in the presence of a copper halide catalyst, to obtain the compound of formula (II).

In a preferred embodiment of the present invention, examples of the copper halide catalyst include, but not limited to, cuprous chloride, cupric chloride, and cuprous bromide, and preferably cuprous chloride. If cuprous chloride is used as a catalyst to prepare a compound of formula (II), the yield of the compound of formula (II) can reach about 96 wt % after the compound of formula (IV) is oxidized for 3 to 4 hours.

In the method of the present invention, the compound of formula (IV) is oxidized generally at 45 to 100° C. In an embodiment of the present invention, the compound of formula (IV) is oxidized at 50 to 60° C.

In embodiments of the present invention, the copper halide catalyst is added for preparing the compound of formula (II) in an amount of 0.05 to 10 wt %, and preferably 0.05 to 2 wt %, based on the weight of the compound of formula (IV).

Examples

Synthesis Example 1

Preparation of a Compound of Formula (II)

In a high pressure autoclave charged with 100 ml of N,N-dimethylformamide (DMF), 0.1 g of cuprous chloride (CuCl) (1 wt %) was added and stirred continuously for 1 hour. After cuprous chloride was completely dissolved in the DMF solution, 10 g of a compound of formula (IV), which is 2,2',6,6'-tetramethylbiphenol (TMBP, purchased from Songwong Company), was added. Then, oxygen was introduced to perform an oxidation reaction of TMBP for 3 to 4 hours at a temperature of 50 to 60° C. After the reaction was completed, the DMF solution was filtered to obtain a deep red product as the title compound, wherein $R_1$, $R_2$, $R_3$ and $R_4$ are methyl, and the yield was 96%. The product obtained was examined by nuclear magnetic resonance to obtain the following result: $^1$H NMR (δ, D-MeOH): 7.7 (s, 4H), 2.1 (s, 12H)

Synthesis Example 2

Preparation of a Compound of Formula (II)

In a high pressure autoclave charged with 100 ml of N,N-dimethylformamide (DMF), 0.1 g of cupric chloride (CuCl$_2$) (10 wt %) was added and stirred continuously for 1 hour. After cupric chloride was completely dissolved in the DMF solution, 10 g of 2,6-dimethylphenol (2,6-DMP, purchased from Acros Company) was added. Then, oxygen was introduced to perform an oxidative coupling reaction of 2,6-dimethylphenol for 2 to 3 hours at a temperature of 80 to 90° C. After the reaction was completed, the DMF solution was filtered to obtain a deep red product as the title compound, and the yield was 35%.

Synthesis Example 3

Preparation of a Compound of (II)

In an autoclave charged with 100 ml of N,N-dimethylformamide (DMF), 1 g of cupric chloride (10 wt %) was added and stirred continuously for 1 hour. After cupric chloride was completely dissolved in the DMF solution, 10 g of TMBP was added. Then, oxygen gas was introduced to perform an oxidation reaction of TMBP for 7 to 8 hours at a temperature of 50 to 60° C. After the reaction was completed, the DMF solution was filtered to obtain a deep red product, and the yield was 93%.

In synthesis examples 1 and 2, the oxidation reaction using TMBP as starting material can attain a higher product yield than using 2,6-DMP. Further, compared with 2,6-DMP, the required reaction temperature and reaction time are lower and shorter, respectively, when using TMBP. It is known that the reaction time is dependent on the amount of the catalyst and the reaction temperature. Based on the results of synthesis examples 1 and 3 (in which TMBP is used as starting material in both cases), at a given reaction temperature, the reaction time and the amount of catalyst can be shorter and lower, respectively, when using CuCl. Consequently, if TMBP and CuCl are used as starting material and catalyst, respectively, the yield of the compound represented by formula (II) is increased.

Example 1

Preparation of a Phosphorus-Containing Compound of the Present Invention

In 200 ml of dichloromethane, 50 g of a compound of formula (III), which is DOPO purchased from Chuan Fong Chemical Industry Co., Ltd., was dissolved. Then, 50 g of a compound of formula (II) and 2.3 g of triethylamine catalyst were added sequentially. The mixed solution was stirred for 1 hour until its color changed, and then it was allowed to react at 30° C. for 1.5 hours. After the reaction system was gradually cooled to room temperature, the resultant reaction mixture was filtered, followed by removal of the solvent to obtain a yellow, phosphorus-containing compound of formula (I), wherein $R_1$, $R_2$, $R_3$ and $R_4$ are methyl, and the yield was 73%. The product obtained was examined by nuclear magnetic resonance to obtain the following result: $^1$H NMR (δ, D-MeOH): 7-8 (m, 8H), 6.0-6.7 (s, 3H), 1.5-3.0 (s, 12H).

As shown in FIG. 1, the product obtained was further identified by IR. The infrared absorption spectrum has shown the absorption of a phosphorus-oxygen double bond at 1207 cm$^{-1}$, absorption of —CH at 2919 cm$^{-1}$, and absorption of a benzene ring at 1596 cm$^{-1}$ and 1583 cm$^{-1}$.

Example 2

In 50 ml of toluene, 10 g of DOPO was dissolved. Then, 10 g of a compound of formula (II) was added. The mixed solution was stirred for 1 hour until its color changed, and then it was allowed to react at 110° C. for 4 hours. After the reaction system was gradually cooled to room temperature, the resultant reaction mixture was filtered, followed by removal of the solvent to obtain a yellow, phosphorus-containing compound of formula (V):

(V)

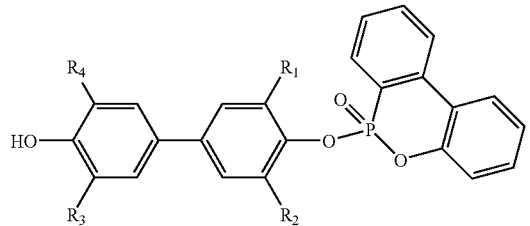

wherein $R_1$, $R_2$, $R_3$ and $R_4$ are methyl, and the yield was 42.3%. The product was examined by nuclear magnetic resonance to obtain the following result: $^1$H NMR (δ, CDCl$_3$): 7.2-8.2 (m, 8H), 7.09 (s, 4H), 4.7-4.9 (s, 1H), 2.26 (s, 12H).

Figure 2:
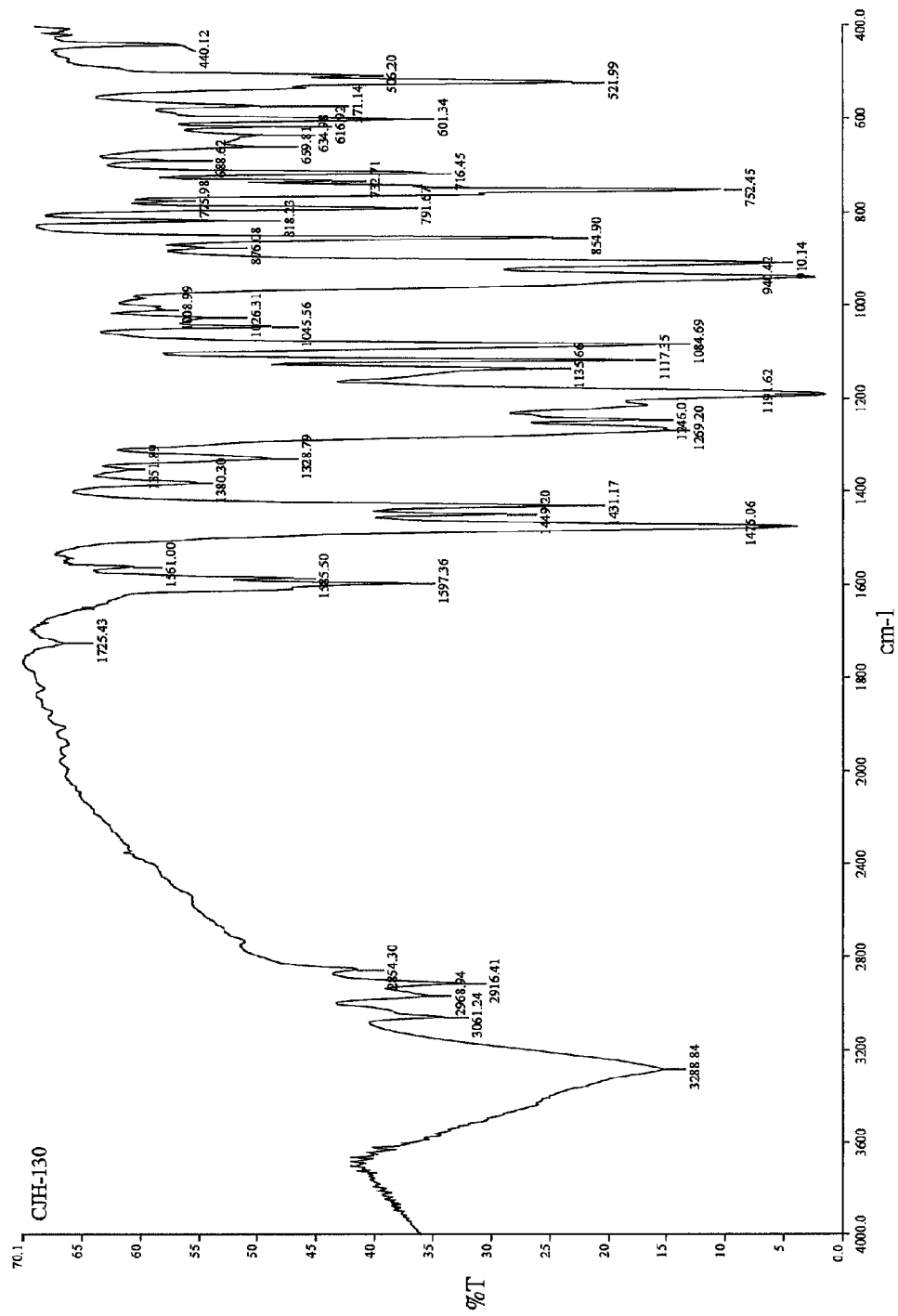
FIG. 2 is an infrared (IR) spectrum of a phosphorus-containing compound of formula (V) according to the present invention.

As shown in FIG. 2, the product obtained was further identified by IR. The infrared absorption spectrum has shown the absorption of a phosphorus-oxygen double bond at 1191 cm$^{-1}$, absorption of —OH at 3288 cm$^{-1}$, absorption of —CH at 2916 cm$^{-1}$ and 2968 cm$^{-1}$, and absorption of benzene ring at 1597 cm$^{-1}$ and 1585 cm$^{-1}$.

In example 2, the phosphorus atom of the compound of formula (III) tends to react with an oxygen atom of the compound of formula (II), at higher temperature and in the absence of an alkaline catalyst, to form a phosphorus-oxygen double bond. On the contrary, in example 1, a phosphorus-containing compound is formed at a lower temperature by adding an alkaline catalyst, such as triethylamine. Further, the alkaline catalyst has the advantage, i.e. releasing the hydrogen atom, which is originally bonded with the phosphorus atom in the compound of formula (III), to increase the nucleophilicity of the compound of formula (III), thereby promoting the reactivity of forming a phosphorus-carbon bond. Thus, increased reactivity leads to increased product yield.

Although there is only a hydroxyl functional group in the phosphorus-containing compound of formula (V), the polycyclic structure, such as DODO group, of the compound has a high char yield as it is burned. Thus, the phophorus-containing compound of formula (V) can be applied to resin curing agents (such as curing agents for epoxy resins), and can also improve flame retardation of resins.

The present invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A phosphorus-containing compound of formula (I):

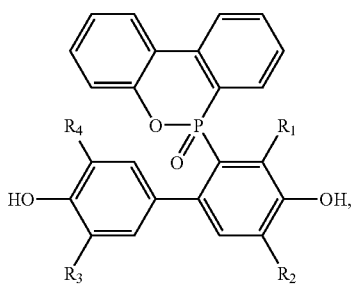

(I)

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy.

2. The phosphorus-containing compound according to claim 1, wherein the $R_1$, $R_2$, $R_3$ and $R_4$ are methyl.

3. A method for preparing a phosphorus-containing compound of formula (I):

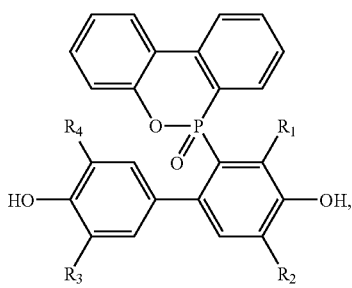

(I)

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy, comprising the step of:

reacting a compound of formula (II):

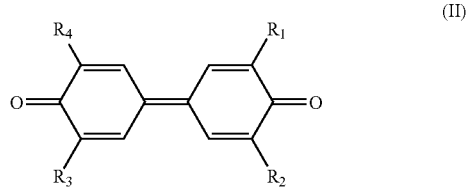

(II)

with a compound of formula (III):

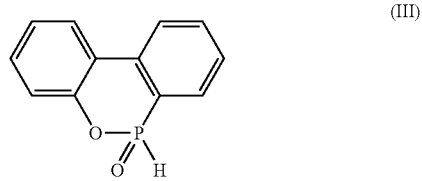

(III)

in the presence of a catalyst and an organic solvent.

4. The method according to claim 3, wherein the catalyst is an alkaline catalyst.

5. The method according to claim 3, wherein the catalyst is one selected from the group consisting of triethylamine, tripropylamine, triphenylphosphine, potassium tert-butoxide (KOt-Bu), and 1,8-diazabicyclo[5.4.0]undec-7-ene.

6. The method according to claim 3, wherein the compound of formula (II) reacts with the compound of formula (III) for 1 to 4 hours.

7. The method according to claim 3, wherein the compound of formula (II) reacts with the compound of formula (III) at a temperature of 25 to 100° C.

8. The method according to claim 7, wherein the compound of formula (II) reacts with the compound of formula (III) at a temperature of 30 to 50° C.

9. The method according to claim 3, wherein the compound of formula (II) is obtained by oxidizing a compound of formula (IV):

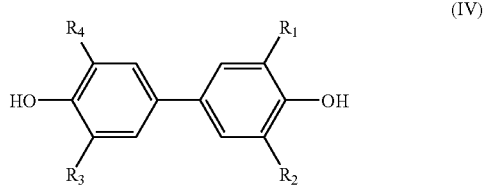

(IV)

for 3 to 8 hours in the presence of a copper halide catalyst.

10. The method according to claim 9, wherein the copper halide catalyst is one selected from the group consisting of cuprous chloride, cupric chloride, and cuprous bromide.

11. The method according to claim 10, wherein the copper halide catalyst is cuprous chloride.

12. The method according to claim 11, wherein the compound of formula (II) is obtained by oxidizing the compound of formula (IV) for 3 to 4 hours in the presence of cuprous chloride.

13. The method according to claim 9, wherein the compound of formula (IV) is oxidized at a temperature of 45 to 100° C.

14. The method according to claim 9, wherein the compound of formula (IV) is oxidized at a temperature of 50 to 60° C.

15. The method according to claim 3, wherein the organic solvent is one or more selected from the group consisting of toluene, dichloromethane, trichloromethane, tetrahydrofuran, xylene, benzene, and N,N-dimethylformamide.

16. The method according to claim 9, wherein the copper halide catalyst is added in an amount of 0.05 to 10 wt % based on a weight of the compound of formula (IV).

17. The method according to claim 16, wherein the copper halide catalyst is added in an amount of 0.05 to 2 wt % based on a weight of the compound of formula (IV).

18. A phosphorus-containing compound of formula (V):

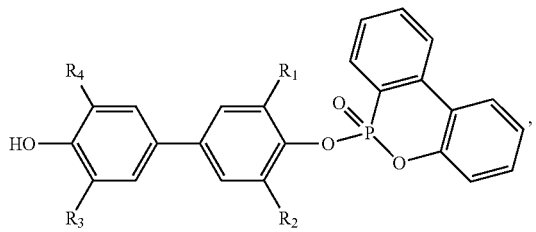

(V)

wherein $R_1$, $R_2$, $R_3$ and $R_4$ are the same or different; and $R_1$, $R_2$, $R_3$ and $R_4$ are independently selected from the group consisting of hydrogen, halogen, $C_{1-8}$ alkyl, haloalkyl, and alkoxy.

19. The phosphorus-containing compound according to claim 18, wherein the $R_1$, $R_2$, $R_3$ and $R_4$ are methyl.

* * * * *